United States Patent
Lomans et al.

(10) Patent No.: US 6,855,704 B2
(45) Date of Patent: Feb. 15, 2005

(54) PROCESS FOR ISOLATING CONJUGATED ESTROGENS

(75) Inventors: John Lomans, Middleburgh, NY (US); Carmen Leiva-Paredes, Schoharie, NY (US)

(73) Assignee: APR LLC, Upper Saddle River, NJ (US)

( * ) Notice: Subject to any disclaimer, the term of this patent is extended or adjusted under 35 U.S.C. 154(b) by 167 days.

(21) Appl. No.: 10/266,754

(22) Filed: Oct. 9, 2002

(65) Prior Publication Data

US 2004/0072812 A1 Apr. 15, 2004

(51) Int. Cl.[7] .............................................. A61K 31/56
(52) U.S. Cl. ..................................................... 514/170
(58) Field of Search ......................................... 514/170

*Primary Examiner*—Barbara P. Badio

(57) ABSTRACT

The present invention relates to a process for extracting conjugated estrogens from pregnant mare urine. The present invention further relates to a process for obtaining a natural mixture of conjugated estrogens. The mixture of conjugated estrogens can be used to prepare products for estrogen replacement therapy or hormone replacement therapy. More specifically, the process for extracting conjugated estrogens from PMU comprises the steps of (a) contacting a mare urine material (MUM) with a resin to adsorb phenolic components, (b) contacting the phenolics-depleted MUM of step (a) with a resin to adsorb the stone and equilin, the major estrogen components, (c) containing the major estrogen-depleted MUM of step (b) with a resin to adsorb the minor estrogen components, (d) separately desorbing the major estrogen components and the minor estrogen components from the resins used in steps (b) and (c), and (e) separately treating the desorbed material form step (d) to obtain crystals of the major estrogen components and the minor estrogen components.

36 Claims, 3 Drawing Sheets

Raw Pegnant Mare Urine (PMU)

↓

Adjust PMU pH to 9.6 – 10.0

↓

Filter through basket filter, 5 µM pore size

↓

Filter through basket filter, 0.1 µM pore size

↓

Mare Urine Material

FIGURE 1

PROCESS FOR ISOLATING CONJUGATED ESTROGENS

BACKGROUND OF THE INVENTION

The present invention relates to a process for extracting conjugated estrogens from pregnant mare urine. The present invention further relates to a process for obtaining a natural mixture of conjugated estrogens. The mixture of conjugated estrogens can be used to prepare products for estrogen replacement therapy or hormone replacement therapy.

The publications and other materials used herein to illuminate the background of the invention, and in particular, cases to provide additional details respecting the practice, are incorporated herein by reference, and for convenience, are referenced by author and date in the following text and respectively grouped in the appended Bibliography.

Menopause is generally defined as the last natural menstrual period and is characterized by the cessation of ovarian function, leading to the substantial diminution of circulating estrogen in the bloodstream. Menopause is usually identified, in retrospect, after 12 months of amenorrhea. It is not a sudden event, but is often preceded by a time of irregular menstrual cycles prior to eventual cessation of menses. Following the cessation of menstruation the decline in endogenous estrogen concentrations is typically rapid. There is a decrease in serum estrogens from circulating levels ranging from 40–250 pg/mL of estradiol and 40–170 pg/ml of estrone during ovulatory cycles to less than 15 pg/mL of estradiol and 30 pg/mL of estrone in postmenopausal women.

As these estrogens decline during the time preceding (perimenopuase) and following the menopause (postmenopause), various physiological changes may result, including vulvar and vaginal atrophy causing vaginal dryness, pruritus and dysparenuia, and vasomotor instability manifested as hot flushes. Other menopausal disturbance may include depression, insomnia, and nervousness. The long-term physiologic effects of postmenopausal estrogen deprivation may result in significant morbidity and mortality due to increase in the risk factors for cardiovascular disease and osteoporosis. Menopausal changes in blood lipid levels, a major component of the pathogenesis of coronary heart disease (CHD), may be precursors to increased incidence of ischemic heart disease, atherosclerosis, and other cardiovascular disease. A rapid decrease in bone mass of both cortical (spine) and trabecular (hip) bone can be seen immediately after the menopause, with a total bone mass loss of 1% to 5% per year, continuing for 10 to 15 years.

Estrogen replacement therapy (ERT) is beneficial for symptomatic relief of hot flushes and genital atrophy and for prevention of postmenopausal osteoporosis. ERT has been recognized as an advantageous treatment for relief of vasomotor symptoms. There is no acceptable alternative to estrogen treatment for the atrophic changes in the vagina; estrogen therapy increases the vaginal mucosa and decreases vaginal dryness. Long term ERT is the key to preventing osteoporosis because it decreases bone loss, reduces spine and hip fracture, and prevents loss of height. In addition, ERT has been shown to be effective in increasing high density Lipoprotein-cholesterol (HDL-C) and in reducing low density lipoprotein cholesterol (LDL-C), affording possible protection against CHD. ERT also can provide antioxidant protection against free radical mediated disorders or disease states. Estrogens have also been reported to confer neuroprotection, and inhibit neurodegenerative disorders, such as Alzheimer's disease. The best known oral estrogen replacement therapy available in the United States is a natural mixture of conjugated equine estrogens sold under the trademark Premarin.

To minimize the occurrence of estrogen-related side effects and to maximize the benefit-risk ratio, the lowest dose effective in relief of symptoms and prevention of osteoporosis should be used. Although ERT reduces the relative risk for ischemia heart disease and osteoporosis, the relative risk of endometrial cancer for postmenopausal women with a uterus may be increased. There are extensive clinical data showing that the relative risk of endometrial cancer can be reduced by the addition of a progestin, either sequentially or continuously. The addition of a progestin to estrogen therapy prevents estrogen-induced endometrial proliferation. Continuous combined hormone replacement therapy (HRT), with appropriate dose of daily estrogen and progestin, has been shown to be effective in relieving vaginal atrophy and vasomotor symptoms, preventing postmenopausal osteoporosis, and reducing the risk of endometrial cancer by prevention of endometrial hyperplasia. See for example, U.S. Published Patent Application No. 20010034340.

As noted, natural mixtures of conjugated estrogens such as are found in the urine of pregnant mares have proved particularly effective and well tolerated for ERT and HRT. The dissolved solids content in the urine of pregnant mares (i.e., pregnant mare urine; PMU) may naturally vary within wide ranges, and may generally lie in a range of 40–90 g dry matter per liter. In addition to urea and other usual urine contents, phenolic constituents are contained in the solids content of the PMU in quantities of about 2%–5% by weight related to dry matter. These phenolic constituents include cresols and dihydro-3,4-bis[3-hydroxyphenyl)methyl]-2 (3H)-furanone (HPMF). These phenolics may be present in free or conjugated form. The PMU contains a natural mixture of estrogens which is largely present in conjugated form, e.g. as sulfuric acid semi-ester sodium salt (referred to hereinafter as "sulfate salt"). The content of conjugated estrogens (calculated as estrogen sulfate salt) may be between 0.3% and 1% by weight relative to dry matter.

Usually extracts containing conjugated estrogens are obtained from the PMU by extraction with a polar organic solvent which is immiscible, or only slightly miscible, with water, such as ethyl acetate, n-butanol or cyclohexanol. In such liquid-liquid extractions, however, a number of problems occur, such as severe foaming, sedimentation, emulcification and poor phase separation. Generally several extraction steps are required, which results in losses and only partial recovery of the estrogen content.

Conjugated estrogens have been isolated by extracting PMU and an organic solvent such as n-butanol or instead by adsorption on charcoal. Such methods have involved a multiplicity of individual process operations, involving back extraction and repeated transfer between n-butanol and aqueous solutions. Such repeated extractions generally result in losses of conjugated estrogens and thus only partial recovery of the estrogen content of the PMU. Examples of an extraction process are discloses in U.S. Pat. Nos. 2,696,265; 2,711,988 and 2,834,712.

In 1968 it was proposed by Bradlow (1968) to use Amberlite XAD-2, a neutral, non-polar hydrophobic polystyrene resin, manufactured by Rohm and Haas, for extraction of conjugated estrogens from urine. The adsorption capacity given is low. According to Bradlow, an optionally diluted urine is passed through a column containing the resin at a low rate of flow. The estrogens are eluted with methanol or ethanol.

Other solid phase extractions of conjugated estrogens from PMU have been described in U.S. Pat. Nos. 3,769,401, 5,723,454 and 5,814,624. In U.S. Pat. No. 3,769,401, a polyamine anion exchange resin, such as Dowex 1-x-2, is used for extracting conjugated estrogens from PMU. The conjugated estrogens adsorbed on the column is eluted with methanol. U.S. Pat. No. 5,723,454 describes the use of a semi-polar polymeric adsorber resin to extract conjugated estrogens from filtered PMU. The adsorbed conjugated esters are desorbed with a water-miscible organic solvent, such as ethers, aliphatic alcohols or ketones. The resin is a porous organic non-ionic polymer, such as a cross-linked aliphatic polycarboxylic acid ester resin, such as Amberlite XAD-7 polyacrylic acid ester resin. U.S. Pat. No. 5,814,624 discloses the use of hydrophobized silica gel, also known as reverse-phase silica gel, to adsorb conjugated estrogens from PMU. The adsorbed conjugated esters are desorbed with a water-miscible organic solvent, such as ethers, alcohols or ketones.

Despite all the past activity in this field, there has remained a need in the art for a more effective way to recover estrogens from pregnant mare urine for preparing conjugated estrogen products.

SUMMARY OF THE INVENTION

The present invention relates to a process for extracting conjugated estrogens from pregnant mare urine (PMU). The present invention further relates to a process for obtaining a natural mixture of conjugated estrogens. The mixture of conjugated estrogens can be used to prepare products for estrogen replacement therapy or hormone replacement therapy.

More specifically, the process for extracting conjugated estrogens form PMU comprises the steps of (a) contacting a mare urine material (MUM) with a resin to adsorb phenolic components, (b) contacting the phobic-depleted MUM of step (a) with a resin to adsorb the estrone and equilin, the major estrogen components, (c) contacting the major estrogen-depleted MUM of step (b) with a resin to adsorb the minor estrogen components, (d) separately desorbing the major estrogen components and the minor estrogen components from the resins used in steps (b) and (c), and (e) separately treating the desorbed material from step (d) to obtain crystals of the major estrogen components and the minor estrogen components.

A natural mixture of the conjugated estrogens is prepared by blending the major estrogen component crystals and the minor estrogen components to yield a product meeting the United States Pharmacopeia requirements for conjugated estrogens.

BRIEF DESCRIPTION OF THE FIGURES

FIG. 1 shows a flow chart of a preferred process for obtaining a mare urine material in accordance with the present invention.

DETAILED DESCRIPTION OF THE INVENTION

Figure 2:
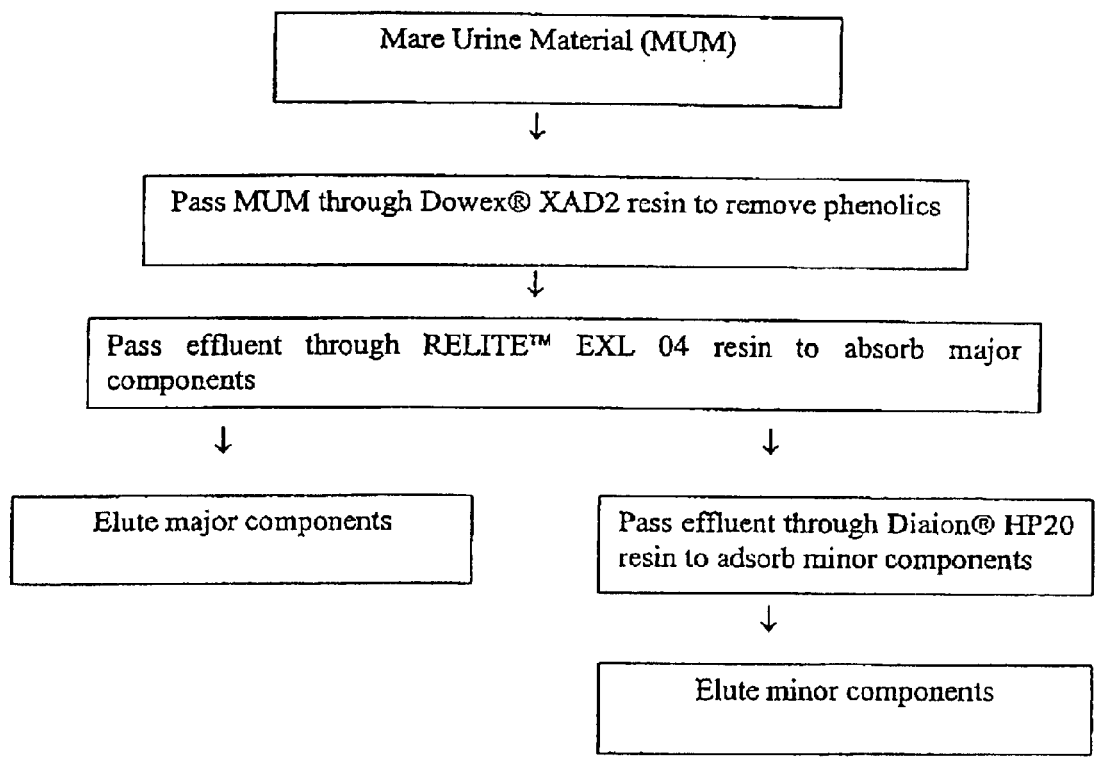
FIG. 2 shows a flow chart of a preferred process for extracting conjugated estrogens from a mare urine material in accordance with the present invention.

The present invention relates to a process for extracting conjugated estrogens from pregnant mare urine. The present invention further relates to a process for obtaining a natural mixture of conjugated estrogens. The mixture of conjugated estrogens can be used to prepare products for estrogen replacement therapy or hormone replacement therapy.

Conjugated estrogens as described in the United States Pharmacopeia 23, National Formulary 18, Official January, 1995 (USP23) is a mixture of sodium estrogen sulfated and sodium equilin sulfate, derived wholly or in part from equine urine or synthetically from estrone and equilin. The most abundant of the estrogens in the standardized blend are the sulfate esters of estrone and equilin. It contains other conjugated estrogenic substances of the type excreted by pregnant mares. Concomitant to the sodium sulfate esters of estrone and equilin are the compounds 17 α-dihydroequilin, 17 β-dihydroequilin and 17 α-estradiol. Signal impurities derived from degradation of the equilin are 17α dihydroequilenin, 17 β-dihydroequilenin and equilenin. Other sodium sulfate esters of steroids that may be present in conjugated estrogens are 17 β-estradiol and $D^{8,9}$-dehydroestrone. Sodium sulfate esters of estrone, equilin and the concomitant components are required by USP23 to present in all dosage forms of conjugated estrogen. These compounds are subject to an upper and lower limit of their concentration.

One example of a conjugated estrogen product for use in estrogen replacement therapy is Premarin (conjugated estrogens tables, (USP) for oral administration that contains a mixture of estrogens obtained exclusively from natural sources, occurring as the sodium salts of water-soluble estrogen sulfated blended to represent the average composition of material derived from pregnant mares' urine. It is a mixture of sodium estrone sulfate and sodium equilin sulfate, and at least the following 8 concomitant components, also as sodium sulfate conjugated: 17 α-dihydroequili, 17 α-estradiol, $D^{8,9}$-dehydroestrone, 17 β-dihydroequilin, 17 β-estradiol, equilenin, 17 α-dihydroequilenin, and 17 β-dihydroequilenin. The make up of Premarin conjugated estrogens is currently being analyzed, and other components are in the process of being identified and characterized. See, for example, Baracat et al (1999) and Dey et al (2000). Premarin conjugated estrogens is indicted in the treatment of moderate to severe vasomotor symptoms associated with the menopause; treatment of vulvar and vaginal atrophy; and prevention of osteoporosis, as well as other indications approved for estrogen products.

In one aspect, the present invention relates to a process for extracting conjugated estrogens from pregnant mare urine. In a second aspect, the present invention relates to a process for obtaining a natural mixture of conjugated estrogens. The mixture of conjugated estrogens can be used to prepare products for estrogen replacement therapy or hormone replacement therapy.

More specifically, the first aspect of the present invention relates to a process for extracting conjugated estrogens from PMU which comprises the steps of (a) contacting a mare urine material (MUM) with a resin to adsorb phenolic components, (b) contacting the phenolic-depleted MUM or step (a) with a resin to adsorb the estrone and equilin, the major estrogen components, (c) contacting the major estrogen-depleted MUM of step (b) with a resin to adsorb the minor estrogen components, (d) separately desorbing the major estrogen components and the minor estrogen components from the resins used in steps (b) and (c), and (e) separately treating the desorbed material from step (d) to obtain crystals of the major estrogen components and the minor estrogen components.

In accordance with the present invention, the first step of the process for extracting conjugated estrogens comprises contacting a mare urine material (MUM) with a resin to remove phenolic components. The MUM is present mare urine(PMU) that has been treated to remove particulate material such as mucilaginous substances and solids. The MUM may further be a concentrate from membrane filtration.

The collected PMU is freed of mucilaginous substances and solids in a known manner. For example, solids and mucilaginous substances are allowed to settle and are then separated by known separation methods, for instance decanting, separation and/or filtration. The PMU can for instance be passed through a known separating apparatus, e.g. a separator, a filtration unit or a sedimenter. A sand bed, for example, may service as a separating apparatus, or commercially-available separator, e.g. nozzle separators or chamber separators, may be used. If desired, a microfiltration apparatus or an ultrafiltration apparatus may also be used, and if they are used it is possible to obtain a substantially bacteria-free and virus-free filter PMU as the same time. This treated PMU can be used as the MUM.

If desired, preservatives, germicides, batericides and/or anthelmintics can be added to the PMU or MUM.

If a concentrated PMU retentate is to be used as the MUM, the retentate may be obtained from the PMU by known membrane filtration. The solids content of the retenate and the composition thereof may vary according to the PMU used and the membrane used for membrane filtration, for instance the pore diameter thereof, and the conditions of the filtration. For instance, when using a nanofiltration membrane, a practically loss-free concentration of the estrogen content in the PMU retentate can be achieved with simultaneous removal of up to 50% by weight of the lower molecular weight PMU contents. PMU retentates which have been concentrated up to a ratio of approximately 1:10, for instance, a ratio of about 1:7, and the volume of which can thus reduced to approximately 1/10, for instance about 1/7, of the original PMU volume, can be used.

In accordance with the preferred embodiment, the MUM is prepared as shown in FIG. 1. The pH of the PMU is first adjusted to between 8.0 and 10.5 with a preferred range of 8.5 to 9.5 to stabilize the sulfonated conjugated estrogens. The use of this pH also breaks down certain proteins and blood products making it easier to filter them during the initial filtration process. The pH adjusted PMU is then filtered through a basket filter having a pore size of between 5–15 micron with a preferred size of 5.0 micron to remove large particulate matter, and subsequently filtered through a basket filter having a pore size of 0.05–0.5 micron with a preferred size of 0.2 micron to remove finer particulate matter. The resulting MUM is collected in a holding tank. It is preferred to use a positive displacement pump to minimize aeration and thereby reduce the possibility of hydrolysis. A flow rate of between 0.5 to 2.00 gallons per minute is utilized. In a more preferred embodiment, the first filtered PMU is pumped through a filter press with a pore size in a range of 0.05–2 micron with a preferred size of 1.0 micron and wherein the filter element is coated with diatomaceous earth before filtering the basket filter having a pore size of 0.1 m.

Therein which is contacted with the MUM is selected such that it will adsorb the phenolic components to remove them form the MUM, but will not adsorb the estrogen components of the MUM. Examples of resins which can be used include non-ionic polystyrene-divinylbenze resins. The MUM is introduced into a column containing the resin and is dept in contact with the resin therein for a sufficient time for adsorption of the phenolic components. Once absorption of the phenolic components on the resin has taken place, the resin laden with the mixture of phenolic components can be separated from the rest of the MUM in a known manner. Advantageously, the MUM can be passed through a column containing the resin at such a flow rate that the contact time is sufficient for adsorption of the phenolic components. It is preferred to pump the MUM through the column. The adsorption of the phenolic components is preferably effected at a temperature range of between 10–20° C. with a preferred temperature of 12° C. It is desired to remove phenolic components at this instance so that they do not interfere with the purification of the conjugated estrogens in the subsequent steps of the process in accordance with the present invention.

It is preferred to use Dowex XAD 2 resin and a glass column that is 6 inches by 8 feet. Dowex XAD2 resin is a non-ionic resin that is a poly-styrene-divinylbenzene (PS-DVD) resin. This resin contains 12% cross-linking and is maintained in the free acid form. The MUM is pumped through the column at a rate of between 0.25–1.5 gallon/min with a preferred rate of 0.75 gallons/min. In a preferred embodiment, the efficiency of the removal of phenolic components is monitored by off-line HPLC determinations made every 2–4, preferably 3 hours, through an analysis of an aliquot of the column effluent.

The resin is regenerated after processing approximately 1000 gallons (3785 liters) of MUM by washing with first purified water, then caustic solution and finally with purified water. The phenolic components are desorbed by the caustic methanolic (50:50 MeOH/NaOH (4%). The solution is subjected to rota-vap until dryness and the residue is stored at 4° C. for further analysis. In the preferred embodiment in which a column is used, the resin is regenerated by first taking the column off line and passing 5–7 column volumes of purified water, pH adjusted to 7, through the column. Subsequently, 7–9 column volumes of 4% caustic solution are applied to the column to desorb (elute) the phenolics from the column. The eluant containing the phenolic components is neutralized and discarded. Finally, 5–7 column volumes of purified water are applied to wash the bed free of residual caustic solution. The column is ready for its next use.

In the second step of the process, the phenolic-depleted MUM from the first step is contacted with a resin to adsorb estrone and equilin, the major estrogen components found in PMU. Thus the resin is selected such that it will adsorb the major estrogen components, but will not adsorb the minor estrogen components. Examples of resins which can be used include weak cationic polystyrene-divinylbenze resins. The phenolic depleted MUM is introduced into a column containing the resin and is kept in contact with the resin therein for a sufficient time for adsorption of the major estrogen components, i.e., estrone and equilin. Once adsorption of the major estrogen components on the resin has taken place, the resin laden with the mixture of major estrogen components can be separated form the rest of the major estrogen-depleted MUM in a known manner. Advantageously, the phenolic-depleted MUM can be passed through a column containing the resin at such a flow rate that the contact time is sufficient for adsorption of the major estrogen components. It is preferred to pump the phenolic-depleted MUM through the column. The adsorption of the major estrogen components is preferably effected at between 10–20° C. with a preferred temperature of 12° C.

It is preferred to use RELITE EXL 04 resin and a glass column 6 inches by 8 feet RELITE EXL 04 resin is a weakly cationic resin that is a polystyrene-divynylbenzene (PS-DVB) resin having sulfate groups. This resin contains 4% cross-linking and is maintained in the weak cationic form. In the preferred embodiment, the effluent from the first step (i.e., the phenolic depleted MUM) is pumped through the column at a rate of between 0.25–1.5 gallons/min with a preferred flow of 0.75 gallon/min. The resin adsorbs estrone and equilin with a high degree of efficiency, while the minor estrogen components pass through the column with minimal adsorption. In the preferred embodiment, the effluent from the first step is passed through the column in the second step until there is no evidence of estrone/equilin in the column effluent as determined by HPLC analysis.

In the third step of the process, the major-estrogen-depleted MUM from the second step is contacted with a resin to adsorb the minor estrogen components found in PMU. Thus the resin is selected such that it will adsorb the minor estrogen components. Examples of resins which can be used include macroporous polystyrene-divinylbenze resins. The major estrogen-depleted MUM is introduced into a column containing the resin and is kept in contact with the resin therein for a sufficient time for adsorption of the minor estrogen components. Once adsorption of the minor estrogen components on the resin has taken place, the resin laden with the mixture of minor estrogen components can be separate form the rest of the minor estrogen-depleted MUM in a known manner. (Advantageously, the major estrogen-depleted MUM can be passed through a column containing the resin at such a flow rate that the contact time is sufficient for adsorption of the major estrogen components). It is preferred to pump the major estrogen-depleted MUM through the column. The adsorption of the major estrogen components is preferably effect at a temperature range of 10–20° C. with a preferred temperature of 12° C.

It is preferred to use Diaion HP20 resin and a glass column 6 inches by 8 feet. Diaion HP20 resin is a non-ionic resin that is a macroporous polystyrene-divynylbenzene (PS-DVB) resin that is completely non-ionic. In the preferred embodiment, the effluent from the second step (i.e., the major estrogen-depleted MUM) is pumped through the column at a flow rate of between 0.25–1.5 gallon/min with a preferred ratio of 0.75 gallon/min. In the preferred embodiment, the effluent from the second step is passed through the column in the third step until there is no evidence of minor estrogen components in the column effluent as determined by HPLC analysis.

In the fourth step of the process, the major estrogen components and the minor estrogen components are separately desorbed from the respective resins. In each instance the estrogen components are desorbed by contacting the estrogen laden resin with a quantity of elution liquid sufficient for elution of the major estrogen components or the minor estrogen components from the resin. Once elution of the major estrogen components or the minor estrogen components has taken place, the resin can be separated form the elution liquid in a known manner. Advantageously, the elution liquid can be passed through a column containing the major or minor estrogen component-laden resin at such a flow rate that the contact time is sufficient for reabsorption of the major or minor estrogen components. It is preferred to pump the elution liquid through the column. Advantageously, the desorption of the major or minor estrogen components is effected at temperature range of 10–20° C. with preferred temperature of 12° C. The eluant containing the major estrogen components and the eluant containing the minor estrogen components are separately stored at a temperature in the range of about 1° C. to about 10° C., preferably about 3° C. to about 7° C., most preferably about 5° C. The quantitative composition of each individual eluant is determined by HPLC analysis.

The eluation liquid comprises use-and/or change as appropriate a water-miscible organic solvent selected from the group consisting of water-miscible ethers, lower aliphatic alcohols and lower aliphatic ketones or a mixture of such a water-miscible organic solvent and water which has optionally been rendered alkaline. Suitable ether constituents to the elution liquid include water-miscible cyclic ethers such as tetrahydrofuran or dioxane, but also miscible open-chain ethers such as lower alkyl ethers with 1–5 carbons in each alkyl group, ethylene glycol diethyl ether (=monoglyme), diethylene glycol dimethyl ether (=diglyme) or ethyloxyethyloxy ethanol=Carbitol). Suitable lower alcohols include water-miscible alkyl alcohols with 1 to 5, preferably 1 to 4, carbon atoms, in particular ethanol or isopropanol. Suitable lower aliphatic ketones include water-miscible ketones with 1 to 5 carbon atoms in each alkyl group, in particular acetone. Elution liquids in which the organic solvent is methanol have provided particularly advantageous. Advantageously mixtures of one of the aforementioned water-miscible organic solvents and water which has optionally been rendered alkaline are used as elution liquids. The pH value of such water containing eluents is in the neutral to alkaline range up to pH 13 and may advantageously be approximately 10 to 12. A solvent which is stable in the pH range used is selected as the solvent component in the water-containing elution liquid. In water-containing alkaline elution liquids having pH values of approximately 10 to 12, lower alcohols preferably methanol are particularly suitable as solvent components. The desired pH value of the water-containing eluents is achieved by adding a corresponding quantity of a water-soluble inert basic substance, preferably an inorganic base, for instance in alkali metal or alkaline earth metal, hydroxide, in particular sodium hydroxide. In water-containing elution liquids there may be a volume ratio of water-miscible organic solvent to water in the range of 30:70 to 60:40 preferably approximately to 50:50.

In the preferred embodiment, the estrogen components are desorbed from the respective estrogen-laden resins by passing 3–10, preferably 5–7; column volumes of the elution liquid through the columns containing the estrogen-laden resins. The preferred elution liquid is an aqueous solution of 4% NaOH and a lower aliphatic alcohol preferably isopropyl alcohol or methanol. In the preferred embodiment, the elution liquid is pumped through the column at a flow rate of 0.15–0.75 gallon/min, preferred 0.25 gallon/min. The eluents are collected as interval samples, e.g., amounts of 10 mL of sample is collected every 2 hours until not any more conjugated estrogen is observed on the HPLC. All of the interval samples, for the eluents of both the major estrogen components and the minor estrogen components, are labeled and individually stored at about 5° C. The quantitative composition of each individual interval sample is determined by HPLC analysis.

Once the major estrogen components and the minor estrogen components have been desorbed, the resin is regenerated after processing approximately 1000 gallons (3785 liters) of phenolic-depleted MUM or major estrogen-depleted MUM, as appropriate, by washing with first purified water, then caustic solution and finally with purified water. In the preferred embodiment in which a column is used, each resin is regenerated by first taking the column off line and passing 5–7 column volumes of purified water, pH adjusted to 7, through the column. Subsequently, 7–9 column volumes of 4% caustic solution are applied to the column. This eluant is neutralized and discarded. Finally, 5–7 column volumes of purified water are applied to wash the bed free of residual caustic solution. The columns are ready for its next use.

A preferred process for extracting the major and minor estrogen components from a mare urine material in accordance with the present invention and as described herein is shown in FIG. 2.

The eluants collected for the major and minor components are separately concentrated. The eluants are concentrated using conventional techniques. It is preferred to concentrate the eluants in a rota-vap under a vacuum of 10 mm Hg or less with the temperature not exceeding 40° C. Each eluant is concentrated until a very viscous, dark liquid residue is obtained. The vacuum is then removed and a lower aliphatic ketone is added to the viscous, dark residue. Suitable lower aliphatic ketones include 1 to 5 carbon atoms in each alkyl group. Acetone is particularly preferred. Generally 0.5–1.0 L, preferred 0.75 of ketone, preferably acetone, at a temperature in the range of 20–40° C., preferred 30° C. is added to the residue. The sample was extracted with acetone, until no more product or color was observed on the ketone layer. Each mixture is then filtered through diatomaceous earth. Each filtrate is collected, and the residues remaining on the filters are discarded. The filtrate for the major estrogen components and the filtrate for the minor estrogen components are separately stored at a temperature in the range of about 1° C. to about 10° C., preferably about 3° C. to about 7° C., most preferably about 5° C.

The acetone filtrates containing the major estrogen components and the minor estrogen filtrates are separately concentrated using conventional techniques. It is preferred to concentrate the filtrates in a rota-vap under a vacuum of 10 mm Hg or less with the temperature not exceeding 40° C. Each filtrate is concentrated until heavy black mass remains. The vacuum is then removed. Each black mass is dissolved in purified water and NaCl is added until saturation, followed by addition of n-butanol. A plurality of extractions is accomplished until no additional product is evident. The n-butanol is carried out at room temperature of between 18–25° C. Any lower, aqueous layer is removed and discarded. The respective n-butanol layers containing the estrogen components are separately evaporated to dryness to produce a dark brown powder containing either the major estrogen components or the minor estrogen components. The dark brown powders are hydroscopic. It is preferred to evaporate the n-butanol layers in a rota-vap under a vacuum of 10 mm Hg or less with the temperature not exceeding 40° C. The dark brown products are separately washed with warm toluene or hexane. Generally 500 mL of toluene or hexane is used to wash the residue at a temperature in the range of 25–45° C, preferred 35 ° C, is added to the powder. The toluene or hexane removes free estrogens and HPLC peak 39 which appears to a degradation product from PMU.

The two residues enriched in either the major estrogen components or the minor estrogen components are separately dissolved in warm acetonitrile ($CH_3CN$). Generally, 200–500 mL of acetonitrile ($CH_3CN$), preferred 300 mL is added to the residue at a temperature in the range of between 20–40° C., with 30° C. being preferred, is added to the powder. The solutions are stored at a temperature in the range of about 1° C. to about 10° C., preferably about 3° C. to about 5° C. for about 24–36 hours. Each solution is separately evaporated under reduced pressure to yield light brown crystals. The crystalline materials from different lots are appropriately labeled as major or minor estrogen components and stored at a temperature in the range of about 1° C. to about 10° C., preferably bout 3° C. to about 5° C., most preferably about 4° C.

Figure 3:
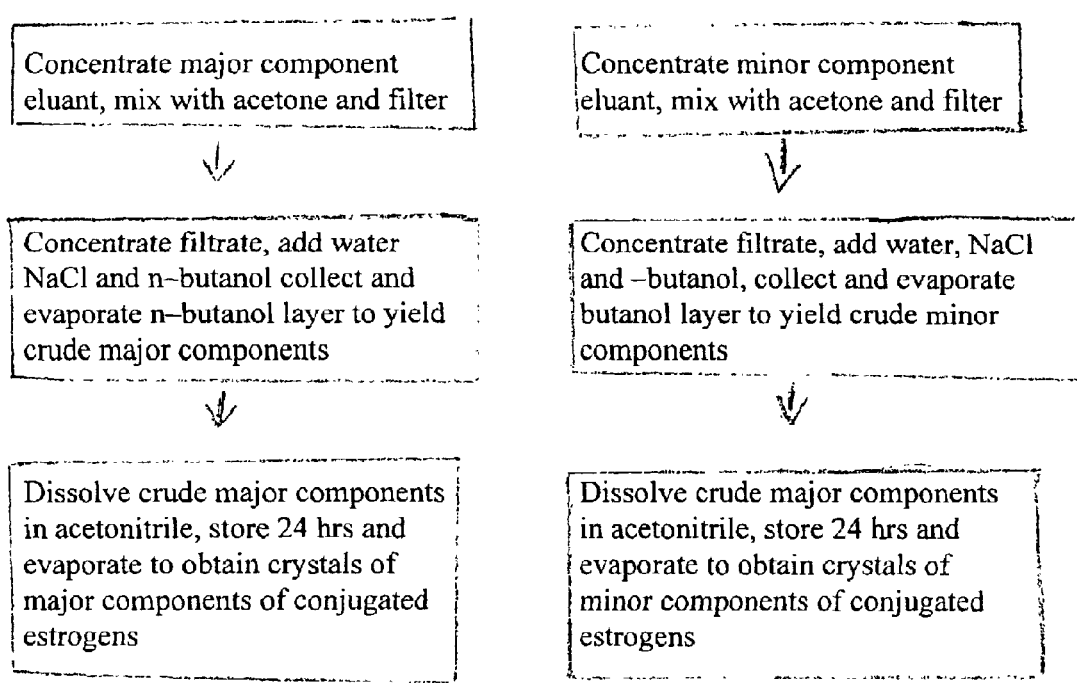
FIG. 3 shows a flow chart of a preferred process for treating the eluants containing the major estrogen components and the minor estrogen components to obtain purified crystals of each.

A preferred process for treating the major and minor estrogen component eluants to obtain crystals of the major estrogen components and crystals of the minor estrogen components in accordance with the present invention and as described herein is shown in FIG. 3.

In a second aspect, the present invention relates to a process for obtaining a natural mixture of conjugated estrogens. The conjugated estrogen product may meet the requirements of USP23, or it may meet the requirements of the FDA Guidance for Industry Conjugated Estrogens, USP-LC, MS Method for Quantitative Chemical Characterization and Documentation of Qualitative Pharmaceutical Equivalence, dated March 2000 ("FDA Guidance"), or it may meet the component profile of the Premarin conjugate estrogens as determined by gas and liquid chromatographic techniques (FDA Guidance). In accordance with this aspect of the invention, sub-batches of the major and minor estrogen components are prepared as described above from different urine shipments, each of which is harvested at different intervals during a gestation period of the mares. Each sub-batch is analyzed for individual compounds using conventional techniques, and the data is stored in a spread sheet. From the analysis of this collective data, a blending procedure is performed to produce a natural component mixed active ingredient which meets the requirements of USP23, the FDA Guidance or the component profile of the Premarin conjugate estrogens.

The conjugated estrogens product (also simply referred to herein as conjugated estrogens in accordance with USP23 produced in accordance with the present invention can be either formulated alone for estrogen replacement therapy or formulated with other active agents, e.g., progestogen, such as medroxyprogesterone acetate (MPA), or androgens, such as testosterone, for hormone replacement therapy. When formulated with other active agents, the conjugated estrogens and other active agents can be formulated as separate tablets or as a unitary combination table.

Tablets containing the conjugated estrogens alone or in combination with other active agents can be prepared as described in U.S. Published Patent Application No. 20010034340, including the patents cited therein. Alternatively, controlled release tablets containing the conjugated estrogens alone or in combination with other active agents can be prepared as described in U.S. Pat. No. 5,908,638.

Either the conjugated estrogens or the components or the combination, including the conjugated estrogens, may be formulated neat or may be combined with one or more pharmaceutically acceptable carriers for administration. For example, solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included such as flavoring agents, coloring agents, preserving agents, and antioxidants, for example, vitamin E, ascorbic acid BHT and BHA.

Conjugated estrogens can be incorporated in granules, spheroids or other multiparticulate forms, and, if necessary, coated to provide adequate stability. These multipaticulates can be combined with other active agents if desired, in the appropriate proportions, with a powder blend, granulation or multiparticulates containing the other active agents and incorporated into hard gelatin capsules.

The preferred pharmaceutical compositions from the standpoint of ease of preparation and administration are solid compositions, particularly tablets and hard-filled or liquid-filled capsules. Oral administration is preferred.

The conjugated estrogens alone or in combination with other active agents can be provided as pharmaceutical dose pack containing any number of daily pharmaceutical dosage units. Preferably, and conventionally, the pack contains 28 tablets or multiples thereof. The pack should indicate that the dosage units are to be taken consecutively on a daily basis until the treatment period has ended, or until the pack has been completed. The next pack should be started on the next consecutive day. For combinations containing a unitary dosage tablet containing, it is preferable that the pack contain one table corresponding to each day of administration. For combinations containing separate dosage units of conjugated estrogens and other active agents, it is preferable that each one tablet of each corresponds to each given days administration, as indicted on the pill pack.

EXAMPLES

The present invention is further detailed in the following Examples, which are offered by way of illustration and are not intended to limit the invention in any manner. Standard techniques well known in the art or the techniques specifically described below are utilized.

Example 1

Overall PMU Evaluation

Three samples of PMU were colleted and analyzed using conventional techniques. Table 1 summarizes the results of this analysis.

TABLE 1

Analysis of PMU Samples

| Analysis | Sample 1 | Sample 2 | Sample 3 |
|---|---|---|---|
| pH | 8.2 | 8.5 | 8.1 |
| Weight % by Dry Weight Estrogen | 7.4 | 7.7 | 7.5 |
| Sulfate Content[1] | 0.257 (70.54) | 0.294 (77.68) | 0.302 (79.79) |
| Cresol Content[1] | 0.80 (211.35) | 0.79 (208.72) | 0.85 (224.57) |
| HpMF[1,2] | 0.262 (68.96) | 0.266 (70.28) | 0.271.71.58 |

[1]Expressed g/gal with mg/1 in parentheses
[2]HPMF is dihydro-3,4-bis(3-hydroxypheny)methyl-2,(3H)-furanone It can be observed from Table 1 that the approximate yield of estrogen sulfate content is in the range of 0.257–0.302 g/gallon (70.54 mg/1–79.79 mg/1) which translates to about 3500 gallons (13,247.5 liters) of PMU yielding a kilogram of the unpurified material.

Example 2

Stability of Raw PMU

PMU samples collected and stored over a period of about five months were analyzed by an HPLC method. The PMU samples were stored at 2° C. One of the samples was stressed by exposure to temperature of 50° C. for four days and was also analyzed. The detection was at two wavelengths 215 and 235 nm and the components separated by a gradient method with acetonitrile 1% trifluoracetic acid and water: 1% trifluroacetic acid. The column used was Phenomenex ODS-3 250 mm/4.6 mm with 5 m pore size.

The peaks observed up to about 48 minutes in the chromatograms are due to phenolics and blood proteins. The differences observed in chromatograms are due to differing portions of these extraneous components. The reason they differ amongst different lots of the PMU is ascribed to varying feedstock and PMU collection during various stages of the gestation. The conjugated estrogens elute around 49–55 minutes in the chromatograms. The dramatic difference in peak area in the conjugated estrogens and those of the phenolics is due to their respective response factor at the detection wavelengths. The most interesting chromatogram was obtained after storing the PMU at 50° C. for 4 days. It was found that the peaks for the conjugated estrogens disappeared and that the peak for the unconjugated estrogen at 81.3 minutes appears. Also, there is a dramatic drop in the extent of the phenolic content in the PMU. The latter observations is due to precipitation of a significant amount of the solids from PMU upon exposure to the stress conditions describe above.

Example 3

Preparation of MUM

The initial pH of the PMU was between 5.5–8.5. The stored PMU was first treated with a 6 M NaOH solution to control the pH to 8.5–9.5 in order to stabilize the sulfonated estrogens and to break down certain proteins and blood products making them easier to filter out during the initial filtration process The PMU was stirred with a pH meter probe inserted in the urine tank. The solution of NaOH was added in aliquots with concomitant monitoring of the pH.

Using a positive displacement pump to minimize aeration, thereby reducing the possibility of hydrolysis, the pH adjusted PMU was them pumped through a basket filter (5 μm pore size) to remove large particulate matter. Then the PMU was pumped through a filter press with 1 μm pore size filter element coated with Celite diatomaceous earth. The flow rate through the filter was approximately 0.5–2.0 gallons per minute. A final filtering step using a 0.1 μm pore size filter was utilized to removed yet finer particulate matter, and the filtrate was collected in a holding tank.

Example 4

Extraction of Conjugated Estrogens from MUM

A Pulsar pump was then used to pass the MUM from Example 1 through a glass column (6 inch×8 feet) 15.24 cm×2.44 m) packed with a Dowex XAD 2 non-ionic resin, which is a poly styrene-divinylbenzene (PS-DVB) polymer backbone with 12% cross-linking maintained in the free acid form. The purpose of this column was to remove certain phenolic components which may interfere with the collection of estrogens in the subsequent steps. The efficiency of removal of the phenolics was monitored by off-line HPLC determination conducted approximately every three hours through an analysis of aliquot of the column effluent. The column was regenerated after processing approximately 1000 gallons (3785 liters) of PMU. The column was regenerated by first taking the column off line and passing 5–7 column volumes of purified water, pH adjusted to 7, through the column. Subsequently, 7–9 column volumes of a 4% caustic solution were applied to the column to desorb the phenolics from the column. This solution was discarded post-neutralization. Finally 5–7 column volumes of purified water were applied to wash the bed free of the residual caustic solution previously applied. The column was then ready for its next use.

The phenolic-depleted MUM was then pumped through a RELITE EXL 04 packed glass column (6 inch×8 feet) (15.24 cm×2.44 m). This resin was a PS-DVB based polymeric resin which has sulfate groups (weak cationic exchanger), with approximately 3%–4% cross-linking. This resin extracts the estrone and equilin from the PMU with a high degree of efficiency. Estrone and equilin are the two major components in the PMU. The minor components pass through the column with minimal adsorption. The phenolic-depleted MUM was passed through the column until there is no evidence of estrone/equilin in the column effluent. These components were analyzed via HPLC.

The components (estrone/equilin) were extracted form the column in by passing a 4% NaOH/methanol or ethanol in aqueous solution, using approximately 5–7 column volumes. This isolate was collected and stored for further processing. The column was then regenerated in a procedure similar to that described above.

The estrone/equilin-depleted MUM was passed through a Diaio HP 20 packed glass column (6 inch×8 feet) (15.24 cm×2.44 m) Diaion HP 20 is a macroporous PS-DVB, which is completely non-ionic. This column extracts the minor estrogenic compounds of interest from the estrone/equilin-depleted MUM. As described above, the estrone/equilin-depleted MUM was passed through the column until off-line evidence of the elution of minor compounds via HPLC was observed. The minor estrogen compounds were desorbed from the column as described above for estrone/equilin. Column regeneration was accomplished as previously described.

At this point, the extracts obtained were labeled as interval samples. Every such sample (major estrogen components or minor estrogen components) were collected and store separately at a temperature of roughly 5° C. The quantitative composition of the individual interval samples was determined via HPLC.

Example 5

Isolation of Crystals of Conjugated Estrogens

The extracts collected for the major and minor components were separately concentrated in a rota-vap under a vacuum of 10 mm Hg or less, with the temperature not exceeding 40° C. The concentration step was carried out until the residue is a very viscous (dark liquid). The vacuum was then removed and acetone was added to the viscous dark residue. Upon mixing with acetone, there was a color change in the residue which indicates completeness of mixing. Each mixture was then filtered through diatomaceous earth with the filtrate collected, and the remaining residue on the filter discarded. Each filtrate was stored at 5 C.

The filtrates for the major and minor estrogen components were separately evaporated under a vacuum until a heavy black mass remains. Each black mass was then dissolved in purified water, and NaCl was added until saturation, followed by the addition of n-butanol. Each mixture was mixed thoroughly and allowed to stand. The lower aqueous layer was discarded from each. The upper layer (n-butanol) contains the conjugated estrogens. Each n-butanol layer was evaporated via a rota-vap to dryness, to a dark brown powder which is hydroscopic. Each dark brown powder was washed with warm toluene which removes the free estrogens and peak 39 which appears to be a degradation product from the PMU.

The two residues, one enriched in estrone/equilin (major components) and one enriched in minor estrogenic compounds (minor components) were separately dissolved in arm acetonitrile. The solutions were stored in a refrigerator (approximately 3° C.–5° C.) for 48 hours. Each solution was then evaporated under reduced pressure to yield light brown crystals. The crystalline material from the different lots were stored at 4° C. and approximately labeled as major or minor components.

Example 6

Preparation of Conjugated Estrogens Product

Several such iterations/sub-batches of the major and minor components were prepared from different urine shipments, each of which was harvested at different intervals during the gestation period of the mares. Each such sub-batch was analyzed for individual compounds and the data was stored in a spread sheet. From evaluation of this collective data, blending procedure was initiated to produce a natural components mixed active ingredient which mimics the component profile of the reference drug product (e.g., Premarin conjugated estrogens) was determined via gas and liquid chromatographic techniques in accordance with FDA guidance for Industry "Conjugated Estrogens, USP Ly LC, LC-MS Method for quantitative Chemical Characterization and Documentation of Qualitative Pharmaceutical Equivalence, dated March 200 (FDA Guidance).

LC/MS analysis of a lot of Premarin conjugated estrogens (lot #A08775) and a conjugated estrogen drug substance prepared above were analyzed in accordance with the FDA Guidance. The FDA Guidance requires injection of conjugated estrogen standard. Unfortunately, the USP sells only the unconjugated estrogen standards. Therefore, it was decided with analysis, i.e, obtaining relative areas, would be preformed by quantitating against the three major conjugated estrogen components present in each of the samples and run.

The data was collected by injecting samples into an LC and analyzing the resultant effluent by both a UV and MS detector. The MS detector monitored nine masses and two reference masses at 347 and 349 AMU for a given injection. Nine such injections were carried out for each sample. The cumulative nine injections covered "the mass range defined in the FDA Guidance. Each mass spectrum was integrated and the relative peak areas estimated by dividing the area of a peak by the areas of the three major peaks due to m/z at 347 and 39. Also, the relative retention time (RRT) of the peak was calculated relative to m/z 349. A table was generated containing the RRT and the relative areas. It was observed that relative areas of several peaks differed between the two produces. A summary fo the observed MS peaks is presented in Table 2.

TABLE 2

Summary of Peaks Observed for Relative Area % vs. RRT

| % Relative Area | Number of Observed Peaks (raw data) | Number of Peaks Common with Other Source | Number of Peaks Different from Other Source | RRT Decimal Place | Number of Peaks Recalculated Based on Decimal Place Round Off |
|---|---|---|---|---|---|
| Example Lot > 1% | 44 | 29 | 15 | 3 | 42 |
| Premarin ® Lot > 1% | 33 | 25 | 8 | 3 | 32 |
| Example Lot > 0.1% but < 1% | 216 | | | 4 | 87 |
| Premarin ® Lot > 0.1% but < 1% | 190 | | | 4 | 84 |

The relative retention times reported by the LC/MS laboratory is in four decimal places. A 0.01 difference in the relative retention time corresponds to about 19 seconds in retention time difference. This data is based on the 349 peak eluting at about 31 minutes. A change in peak density plotted as a function of rounding off the decimal place was observed. This change in density is more so for the peaks observed, at a level less than 1% relative to the three major peaks. This reduction however does not take into consideration the m/z values for these peaks. Data reduction reveals that there are about 66 peaks that are present in both products for relative area greater than 0.1% but less than 1% of the 347/349 parent peaks.

From the plot of m/z versus the relative area % for peaks greater than 1%, both the products exhibit 21 major m/z. However, the lot according to the present example has seven peaks that are not present in the Premarin lot and the Premarin lot has five peaks that are not present in the lot of the present example. In the case of the Premarin lot's five peaks with area greater than 1% eluting at an RRT of about 0.08 were excluded on the assumption that they are due to excipients in the brand formulation.

In view of this data, it is believed that, based upon the FDA Guidance, a Conjugated Estrogens API prepared in accordance with the present invention should be considered equivalent to or the "same as" Premarin conjugated estrogens API for the purposes of utilization in the development of a therapeutically equivalent generic conjugated estrogens drug product.

In regard to the stated requirement in the FDA Guidance that approximately 21 of 56 AMU's should be observed for which the chromatogram exhibit approximately 40 peaks at greater than or equal to 1.0% area, it can be seen that the API of a conjugated estrogens product prepared in accordance with the present invention is substantially in agreement with the requirement as demonstrated by the data presented in Table 2. Further additional data generated on the brand product demonstrates what appears to be a considerable potential for variability in the brand product in both the absolute number of peaks when view against the FDA Guidance requirement of 21, and the quantitative levels of individual peaks.

While the invention has been disclosed in this patent application by reference to the details of preferred embodiments of the invention, it is to be understood that the disclosure is intended in an illustrative other than in a limiting sense, as it is contemplated that modification will readily occur to those skilled in the art, within the spirit of the invention and the scope of the appended claims.

BIBLIOGRAPHY

Baracat, E., et al (1999) Estrogen activity and novel tissue selectivity of $\Delta^{8,9}$-dehydroestrone sulfate in postmenopausal women. *J Clin Endocrinol Metab* 84:2020–2027.

Bradlow, H. L. (1968) Extraction of steroid conjugates with a neutral resin *Steroids* 11:265–272.

Dey, M. Et al (2000). Recent insights into the varying activity of estrogens. *Maturitas* 34:S25–S33.

United States Pharmacopeia National Formulary 24, 2000 (USP24).

U.S. Pat. No. 5,908,638.

U.S. Published Patent Application No. 20010034340.

What is claimed is:

1. A method for obtaining crude conjugated estrogens from pregnant mare urine containing major conjugated estrogen components and minor conjugated estrogen components comprising:

(a) contacting a mare urine material having a pH of about 8.5 to about 9.5 and freed of particulate matter with a quantity of a non-ionic resin to adsorb phenolic compounds contained in the mare urine material and separating the resin laden with the phenolic compounds from a first residual mare urine material;

(b) contacting the first residual mare urine material with a quantity of weak cationic resin to adsorb the major conjugated estrogen components contained in the mare urine material and separating the resin laden with the major conjugated estrogen components from a second residual mare urine material;

(c) contacting the second residual mare urine material with a quantity of a non-ionic resin to adsorb the minor conjugated estrogen components contained in the mare urine material and separating the resin laden with the minor conjugated estrogen components from a third residual urine material;

(d) contacting the resin laden with the major conjugated estrogen components with a sufficient quantity of an elution liquid selected from the group consisting of isopropyl alcohol and methanol to desorb the adsorbed major conjugated estrogen components and recovering an eluant containing crude major conjugated estrogen components; and (e) contacting the resin laden with the minor conjugated estrogen components with a sufficient quantity of an elution liquid selected from the group consisting of isopropyl alcohol and methanol to desorb the adsorbed minor conjugated estrogen components and recovering an eluant containing crude minor conjugated estrogen components.

2. The method of claim 1, wherein the mare urine material is prepared by adjusting the pH of pregnant mare urine to a pH of about 8.5 about 9.5 with addition of Na OH and filtering the pH adjusted urine to remove particulates.

3. The method of claim 2, wherein the pH adjusted urine is filtered by first a filtration with a filter having a pore size of about 5 µm and a second filtration with a filter having a pore size of about 0.1 µm.

4. The method of claim 3 wherein the urine is filtered through a filter element coated with diatomaceous earth having a pore size of about 1 µm between the first and second filtrations.

5. The method of claim 1, wherein the non-ionic resin in step (a) is a poly styrene-divinylbenzene resin with 12% cross-linking.

6. The method of claim 1 wherein the weak cationic resin in step (b) is a polystyrene-divinylbenzene resin with sulfate groups and bout 3% to about 4% cross-linking.

7. The method of claim 1, wherein the non-ionic resin in step (c) is a macroporous poly styrene-divinylbenzene resin.

8. The method of claim 1 wherein the elution liquid is selected from the group consisting of (a) 4% NaOH methanol in aqueous solution and (b) 4% NaOH in aqueous solution in a ratio of 50:50 MeOH/NaOH (4%).

9. The method of claim 1, wherein the contacting and eluting steps are performed by passing the urine or the elution liquid through a vessel containing the resins.

10. The method of claim 1, further comprising;
(f) concentrating the eluant containing the major conjugated estrogen components to a viscous liquid, mixing the viscous liquid with acetone and filtering the acetone mixture through diatomaceous earth to obtain a filtrate containing crude major conjugated estrogen components; and
(g) concentrating the eluant containing the minor conjugated estrogen components to a viscous liquid, mixing the viscous liquid with acetone and filtering the acetone mixture through diatomaceous earth to obtain a filtrate containing crude minor conjugated estrogen components.

11. The method of claim 10, wherein the mare urine material is prepared by adjusting the pH of pregnant mare urine to a pH of about 8.5 to about 9.5 with addition of NaOH and filtering the pH adjusted urine to remove particulates.

12. The method of claim 11, wherein the pH adjusted urine is filtered by first a filtration with a filter having a pore size of about 5 µm and a second filtration with a filter having a pore size of about 0.1 µm.

13. The method of claim 12, wherein the urine is filtered through a filter element coated with diatomaceous earth having a pore size of about 1 µm between the first and second filtrations.

14. The method of claim 10, wherein the non-ionic resin in step (a) is a poly styrene-divinylbenzene resin with 12% cross-linking.

15. The method of claim 10, wherein the weak cationic resin in step (b) is a poly styrene-divinylbenzene resin with sulfate groups and about 3% to about 4% cross-linking.

16. The method of claim 10, wherein the non-ionic resin in step (c) is a macroporous poly styrene-divinylbenzene resin.

17. The method of claim 10, wherein the elution liquid is selected from the group consisting of (a) 4% NaOH methanol in aqueous solution and (b) 4% NaOH in aqueous solution in a ratio of 50:50 MeOH/NaOH (4%).

18. The method of claim 10, wherein the contacting and eluting steps are performed by passing the urine or the elution liquid through a vessel containing the resins.

19. A method for obtaining conjugated estrogens from pregnant mare urine containing major conjugated estrogen components and minor conjugated estrogen components comprising:

(a) contacting a mare urine material having a pH of about 8.5 to about 9.5 and freed of particulate matter with a quantity of a non-ionic resin to adsorb phenolic compounds contained in the mare urine material and separating the resin laden with the phenolic compounds from a first residual mare urine material;
(b) contacting the first residual mare urine material with a quantity of weak cationic resin to adsorb the major conjugated estrogen components contained in the mare urine material and separating the resin laden with the major conjugated estrogen components from a second residual mare urine material;
(c) contacting the second residual mare urine material with a quantity of a non-ionic resin to adsorb the minor conjugated estrogen components contained in the mare urine material and separating the resin laden with the minor conjugated estrogen components from a third residual urine material;
(d) contacting the resin laden with the major conjugated estrogen components with a sufficient quantity of an elution liquid selected from the group consisting of isopropyl alcohol and methanol to desorb the adsorbed major conjugated estrogen components and recovering an eluant containing crude major conjugated estrogen components;
(e) contacting the resin laden with the minor conjugated estrogen components with a sufficient quantity of an elution liquid selected from the group consisting of isopropyl alcohol and methanol to desorb the adsorbed minor conjugated estrogen components and recovering an eluant containing crude minor conjugated estrogen component;
(f) concentrating the eluant containing the major conjugated estrogen components to a viscous liquid, mixing the viscous liquid with acetone and filtering the acetone mixture through diatomaceous earth to obtain a filtrate containing crude major conjugated estrogen components;
(g) concentrating the eluant containing the minor conjugated estrogen components to a viscous liquid, mixing the viscous liquid with acetone and filtering the acetone mixture through diatomaceous earth to obtain a filter containing crude minor conjugated estrogen components;
(h) evaporating the eluant containing the major conjugated estrogen components to produce a heavy black mass, dissolving the black mass in water, adding NaCl until saturation to produce a solution, mixing the solution with n-butanol, extracting the n-butanol layer, evaporating the n-butanol layer to dryness to produce a powder containing the major conjugated estrogen components, washing the powder with toluene to remove free estrogens and degradation products, dissolving the powder in acetonitrile and removing the acetone to produce crystalline major conjugated estrogen components; and
(i) evaporating the eluant containing the minor conjugated estrogen components to produce a heavy black mass, dissolving the black mass in water, adding NaCl until saturation to produce a powder containing the minor conjugated estrogen components, washing the powder with toluene to remove free estrogens and degradation products, dissolving the powder in acetonitrile and removing the acetonitrile to produce crystalline in or conjugated estrogen components.

20. The method of claim 19, wherein the mare urine material is prepared by adjusting the pH of pregnant mare urine to a pH of about 9.6 to about 10.0 with addition of NaOH and filtering the pH adjusted urine to remove particulates.

21. The method of claim 20, wherein the pH adjusted urine is filtered by first a filtration with a filter having a pore size of about 5 μm and a second filtration with a filter having a pore size of about 0.1 μm.

22. The method of claim 21, wherein the urine is filtered through a filter element coated with diatomaceous earth having a pore size of about 1 μm between the first and second filtrations.

23. The method of claim 19, wherein the non-ionic resin in step (a) is a poly styrene-divinylbenzene resin with 12% cross-linking.

24. The method of claim 19, wherein the weak cationic resin in step (b) is a poly styrene-divinylbenzene resin with sulfate groups and about 3% to about 4% cross-linking.

25. The method of claim 19, wherein the non-ionic resin in step (c) is a macroporous poly styrene-divinylbenzene resin.

26. The method of claim 19, wherein the elution liquid is selected from the group consisting of (a) 4% NaOH/methanol in aqueous solution and (b) 4% NaOH in aqueous solution in a ratio of 50:50 MeOH/NaOH (4%).

27. The method of claim 19, wherein the contacting and eluting steps are performed by passing the urine or the elution liquid through a vessel containing the resins.

28. A method for obtaining a natural mixture of conjugated estrogens from pregnant mare urine containing major conjugated estrogen components and minor conjugated estrogen components comprising;
   (a) contacting a mare urine material having a pH of 8.5 to about 9.5 and freed of particulate matter with a quantity of a non-ionic resin to adsorb phenolic compounds contained in the mare urine material and separating the resin laden with the phenolic compounds form a first residual mare urine material;
   (b) contacting the first residual mare urine material with a quantity of weak cationic resin to adsorb the major conjugated estrogen components contained in the mare urine material and separating the resin laden with the major conjugated estrogen components form a second residual mare urine material;
   (c) contacting the second residual mare urine material with a quantity of a non-ionic resin to adsorb the minor conjugated estrogen components contained in the mare urine material and separating the resin laden with the minor conjugated estrogen components from a third residual urine material;
   (d) contacting the resin laden with the major conjugated estrogen components with a sufficient quantity of an elution liquid selected from the group consisting of isopropyl alcohol and methanol to desorb the adsorbed major conjugated estrogen components and recovering an eluant containing crude major conjugated estrogen components;
   (e) contacting the resin laden with the minor conjugated estrogen components with a sufficient quantity of an elution liquid selected from the group consisting of isopropyl alcohol and methanol to desorb the adsorbed minor conjugated estrogen components and recovering an eluant containing crude minor conjugated estrogen components;
   (f) concentrating the eluant containing the major conjugated estrogen components to a viscous liquid, mixing the viscous liquid with acetone and filtering the acetone mixture through diatomaceous earth to obtain a filtrate containing crude major conjugated estrogen components;
   (g) concentrating the eluant containing the minor conjugated estrogen components to a viscous liquid, mixing the viscous liquid with acetone and filtering the acetone mixture through diatomaceous earth to obtain a filtrate containing crude minor conjugated estrogen components;
   (h) evaporating the eluant containing the major conjugated estrogen components to produce a heavy black mass, dissolving the black mass in water, adding NaCl until saturation to produce a solution, mixing the solution with n-butanol, extracting the n-butanol layer, evaporating the n-butanol layer to dryness to produce a powder containing the major conjugated estrogen components, washing the powder with toluene to remove free estrogens and degradation products, dissolving the powder in acetonitrile and removing the acetonitrile to produce crystalline major conjugated estrogen components;
   (i) evaporating the eluant containing the minor conjugated estrogen components to produce a heavy black mass, dissolving the black mass in water, adding NaCl until saturation to produce a solution, mixing the solution with n-butanol, extracting the n-butanol layer, evaporating the n-butanol layer to dryness to produce a powder containing the minor conjugated estrogen components, washing the powder with toluene to remove free estrogens and degradation products, dissolving the powder in acetonitrile and removing the acetonitrile to produce crystalline minor conjugated estrogen components;
   (i) analyzing the crystalline major conjugated estrogen components to determine the quantity of major conjugated estrogen components present;
   (j) analyzing the crystalline minor conjugated estrogen components to determine the quantity of minor conjugated estrogen components present; and
   (k) blending the crystalline major conjugated estrogen components and the crystalline minor conjugated estrogen components to produce a natural mixture of conjugated estrogens.

29. The method of claim 28, wherein the mare urine material is prepared by adjusting the pH of pregnant mare urine to a pH of about 8.5 to about 9.5 with addition of NaOH and filtering the pH adjusted urine to remove particulates.

30. The method of claim 29, wherein the pH adjusted urine is filtered by first a filtration with a filter having a pore size of about 5 μm and a second filtration with a filter having a pore size of about 0.2 μm.

31. The method of claim 30, wherein the urine is filtered through a filter element coated with diatomaceous earth having a pore size of about 1 μm between the first and second filtrations.

32. The method of claim 28, wherein the non-ionic resin in step (a) is a poly styrene-divinylbenzene resin with 12% cross-linking.

33. The method of claim 28, wherein the weak cationic resin in step (b) is a poly styrene-divinylbenzene resin with sulfate groups and about 3% to about 4% cross-linking.

34. The method of claim 28, wherein the non-ionic resin in step (c) is a macroporous poly styrene-divinylbenze resin.

35. The method of claim 28, wherein the elution liquid is selected from the group consisting of (a) 4% NaOH methanol in aqueous solution and (b) 4% NaOH in aqueous solution in a ratio of 50:50 MeOH/NaOH (4%).

36. The method of claim 28, wherein the contacting and eluting steps are performed by passing the urine or the elution liquid through a vessel containing the resins.

* * * * *